United States Patent [19]

Wells

[11] Patent Number: 5,410,403

[45] Date of Patent: Apr. 25, 1995

[54] PARTICLE MEASURING SYSTEM WITH PUMP ADAPTED TO MAINTAIN CONSTANT FLOW FOR DIFFERENT PRESSURES AND VISCOSITIES

[75] Inventor: David Wells, Silver Spring, Md.

[73] Assignee: Pacific Scientific Company, Newport Beach, Calif.

[21] Appl. No.: 104,896

[22] Filed: Aug. 12, 1993

[51] Int. Cl.6 .................................. G01N 15/02
[52] U.S. Cl. ........................................... 356/335
[58] Field of Search ................ 356/335, 336, 338; 73/53.01, 37.6, 61.48, 61.69

[56] References Cited

U.S. PATENT DOCUMENTS

| | | | |
|---|---|---|---|
| 2,243,074 | 5/1941 | Anderson | 116/125 |
| 2,623,539 | 12/1952 | Lee, II | 137/487 |
| 4,971,527 | 11/1990 | Dick | |
| 5,199,853 | 4/1993 | Padden | 417/43 |

Primary Examiner—Richard A. Rosenberger
Assistant Examiner—Russell C. Wolfe
Attorney, Agent, or Firm—Lane, Aitken & McCann

[57] ABSTRACT

In a particle measuring instrument for measuring particles entrained in liquids, a gear pump located downstream from the flow cell of the particle measuring instrument is used to maintain a constant rate of flow through the flow cell. When the source of liquid is at a high pressure, a pressure regulator and a check valve are used to maintain the pressures at the inlet and outlet sides of the gear pump, respectively, at predetermined pressure values to maintain a predetermined pressure differential across the gear pump. When the source of liquid to be measured is at ambient pressure, the outlet of the gear pump is connected to ambient pressure and the gear pump draws liquid through the flow cell causing the pressure at the inlet side of the gear pump to drop the predetermined pressure differential below ambient pressure.

14 Claims, 1 Drawing Sheet

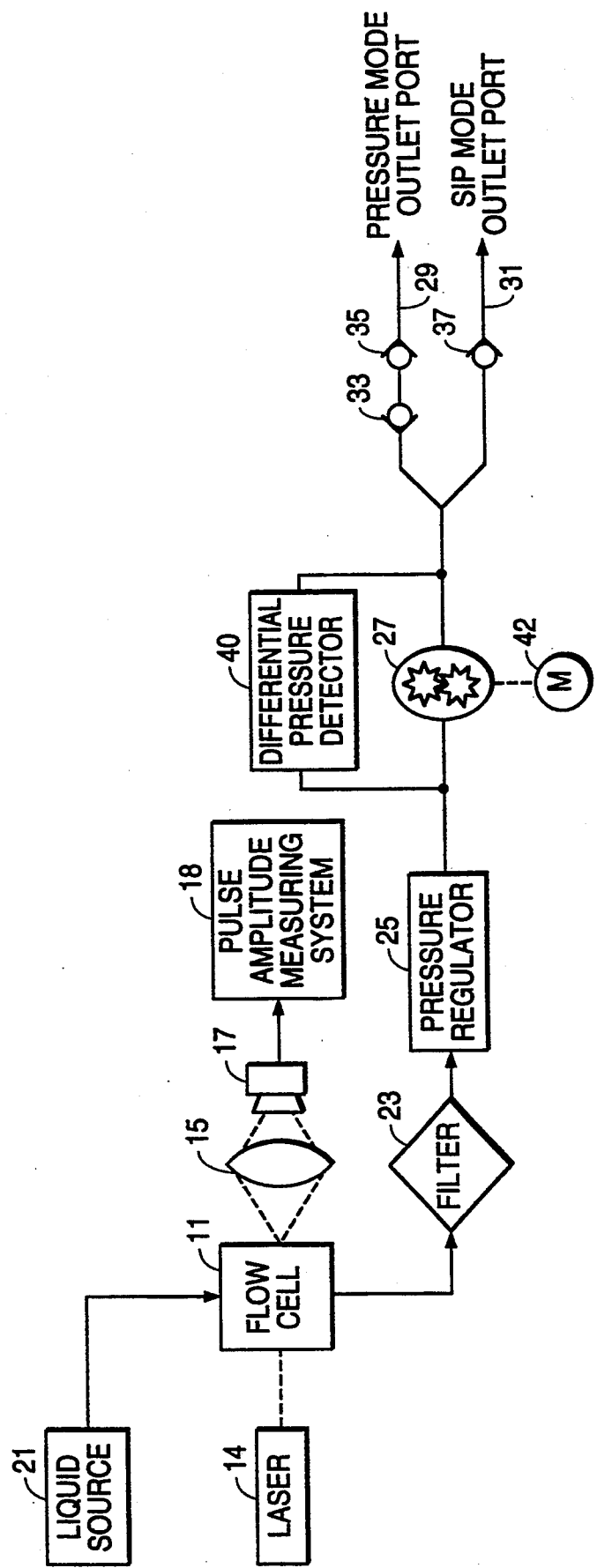

PARTICLE MEASURING SYSTEM WITH PUMP ADAPTED TO MAINTAIN CONSTANT FLOW FOR DIFFERENT PRESSURES AND VISCOSITIES

This invention relates to an instrument for detecting and measuring the size of particles entrained in liquids and more particularly to such an instrument provided with a pump to maintain a constant flow and adapted to maintain constant flow for different pressure and viscosities of the liquid.

BACKGROUND OF THE INVENTION

Particle measuring instruments for measuring particles entrained in liquids, need to maintain a relatively constant rate of flow through the particle sensor of the instrument to achieve accurate and consistent measurement of particle sizes. One way for maintaining a constant flow is to pump the liquid through the particle sensor by means of a positive displacement pump such as a gear pump which if run at a constant rate can achieve a relatively constant rate of flow. However a gear pump is not effective to maintain a sufficiently constant rate of flow when the liquid entraining the particles is at a high pressure or is at relatively high viscosities because these conditions will cause a pressure variation across the gear pump which in turn will cause a variation in the leakage through the gear pump and thus cause a variation in the rate of flow through the sensing instrument.

SUMMARY OF THE INVENTION

The present invention provides a system maintaining a constant rate of flow through the sensor making use of a gear pump to achieve the constant flow. In accordance with the invention, liquid entraining particles, which may be at a high pressure and also may have relatively high viscosity, or may be at ambient or atmospheric pressure, flows first through the particle sensor, then through a pressure regulator and then through the gear pump. From the gear pump, the liquid flows to one of two outlets depending upon whether the source of liquid is at a high pressure or ambient pressure. If the source of liquid is at a high pressure the liquid flows from the gear pump through a check valve which has a 10 psi cracking pressure and then to a "pressure mode" outlet port. When liquid is at ambient pressure, the liquid will flow from the gear pump to a "sip mode" outlet port bypassing the check valve.

When the liquid entraining the particles is at a high pressure the pressure regulator will set the pressure on the inlet side of the gear pump at 8 psi and the check valve will cause the pressure on the outlet side of the gear pump to be maintained at 10 psi. Accordingly, there will be a 2 psi pressure rise across the gear pump which will be constant and independent of the pressure in the liquid source and independent of viscosity of the liquid. As a result the leakage through the gear pump will be a constant known low value related to the 2 psi pressure rise across the gear pump and a constant flow rate will be achieved even though the liquids entraining particles are provided to the system at different pressures and have different viscosities. If the liquid has a high viscosity, then there will be a larger pressure drop through the sensor, but the pressure regulator will maintain the inlet pressure at the gear pump at 8 psi and the check valve will maintain the output pressure at 10 psi. Accordingly for different viscosities the pressure differential across the gear pump will be maintained at 2 psi so that a constant flow rate is maintained for liquids with different viscosities.

When the source of liquid is at ambient pressure the system is operated in the sip mode. In this mode, the pressure in the liquid will drop from ambient in the liquid source to 2 psi below ambient at the inlet to the gear pump due to the flow resistance in this flow path. The outlet of the gear pump will be at ambient pressure due to the connection of the gear pump outlet directly to the sip mode outlet port. Accordingly, the pressure differential across the pump will be maintained at 2 psi and the constant flow rate will be maintained.

BRIEF DESCRIPTION OF DRAWINGS

The single figure of the drawings schematically illustrates the system of the present invention.

DESCRIPTION OF A PREFERRED EMBODIMENT

As shown in the drawings, the particle measuring instrument of the present invention comprises a flow cell 11 through which the liquid entraining particles to be measured is caused to flow. The flow cell 11 may be like that disclosed in copending application Ser. No. 07/973,383 filed Nov. 10, 1982 invented by Gary Morgan et al. A laser 14 directs a light beam through a stream of liquid sample flowing through the flow cell 11. Light scattered from particles entrained in the liquid sample is collected by lens 15 and is detected by a photodetector 17. The pulses generated by the photodetector 17 in response to light scattered from the particles are directed to a pulse measuring system 18 which measures the amplitude of each pulse as a determination of particle size.

The liquid entraining the particles comes from a source 21 which may be at a high pressure or may be at ambient pressure, which will usually be atmospheric pressure. The outlet side of the flow cell connects through a filter 23 and a pressure regulator 25 to the inlet side of a gear pump 27, which is driven at constant speed by motor 42. The filter 23 serves to prevent larger particles entrained in the liquid from passing through the pump 27 and damaging it. The outlet side of the gear pump 27 is connected to "pressure mode" outlet port 29 and "sip mode" outlet port 31. The connection to the outlet port 29 is through a check valve 33 and an outlet valve 35 and the connection to the outlet port 31 is through an outlet valve 37. A differential pressure gauge 40 is connected across the pump 27 to measure and indicate the amount of pressure rise across the pump 27.

When the pressure of the liquid source 21 is at a high value, above 10 psi, the valve 35 will be open and the valve 37 will be closed to operate the system in the pressure mode so that the liquid flows to the outlet port 29 through the check valve 33. The pressure regulator 25 reduces the pressure of the liquid received at its inlet side to 8 psi at its outlet side so that the inlet pressure to the gear pump 27 is 8 psi. The check valve 33 has a cracking pressure of 10 psi so that when the liquid is being directed by valves 35 and 37 to the pressure mode outlet port 29 the outlet pressure of the gear pump 27 is maintained at a pressure of 10 psi by the check valve 33. As a result there will be a 2 psi pressure rise across the gear pump 27 regardless of the value of the high pressure of the source of liquid 21. As a result the leakage through the gear pump will be minimal and the leakage that does occur will be constant. Accordingly the pump 27, being driven a constant speed by motor 42, achieves a constant flow rate through the flow cell 11 for different high pressures in the source of the liquid 21.

When the liquid entraining the particles to be measured has a high viscosity, the source of liquid will be at high pressure in order to cause flow through the flow cell 11 at a satisfactory flow rate. Differences in viscosities will cause differences in the pressure drop through the flow cell and filter and cause variation in the pressure at the upstream side of the pressure regulator 25. The constant flow rate is nevertheless maintained because the pressure regulator 25 will maintain the pressure at the inlet side of the gear pump at 8 psi for the liquids with the different viscosities. The check valve 33 will maintain the pressure on outlet side of the gear pump 27 at 10 psi so that a constant 2 psi differential across the gear pump is maintained and a constant flow rate is achieved in liquids with different viscosities.

When the source of the liquid 21 is at ambient pressure, the system operates in the sip mode in which the valve 35 is closed and the valve 37 is open so that the liquid flows from the outlet of the gear pump 27 to the sip outlet port 31. In this mode of operation, the gear pump 27 draws the liquid through the flow cell 11 and the pressure regulator 25 has no effect on the pressure of the flowing fluid. When the inlet side of the pressure regulator 25 is below 8 psi, it allows the liquid to flow freely therethrough so that the pressure is essentially the same on both sides of the pressure regulator 25. The resistance of the flow path between the liquid source and the gear pump 27 will cause the liquid flowing through this flow path to undergo a pressure drop of 2 psi, most of the drop occurring in the flow cell 11. The pressure drop will be constant because the flow rate is maintained constant and the liquid will have a low viscosity near that of water. As a result the pressure at the inlet of the gear pump 27 will be at 2 psi below ambient pressure in the sip mode of operation. Since in the sip mode, the outlet of gear pump is connected directly to ambient pressure at the sip mode outlet port, the outlet of the gear pump will be at ambient pressure, and accordingly, a differential pressure of 2 psi is provided across the gear pump. As a result the pump 27 will maintain the same desired constant flow rate through the flow cell in the sip mode that it achieves in pressure mode.

In operation, the filter 23 may eventually become clogged and interfere with proper operation of the constant flow system. When the filter becomes clogged, the pressure drop through the filter will increase to cause the pressure at the inlet side of the pump 25 to drop to a low value and cause the pressure across the pump to rise above 2 psi. The pressure gauge 40 will then indicate a pressure greater than 2 psi indicating a malfunctioning of system.

When the system described above operates in the pressure mode, the force that causes the liquid to flow through the flow cell comes from the high pressure of the source of liquid and not from the pump, which in this mode of operation serves only to maintain a constant rate of flow. In the sip mode of operation the pump supplies a suction force to draw the liquid through the flow cell while also maintaining the constant flow rate.

The above described system is designed to operate in two modes, the sip mode and the pressure mode. It will be apparent that if the sip mode is not needed, the connection to the sip mode port could be eliminated. In such a modified system it still would be preferable to have the pump positioned downstream from the flow cell but the pump along with the pressure regulator and check valve could be provided upstream from the flow cell as long as the liquid is not so viscous to cause a pressure drop through the flow cell greater than the cracking pressure of the check valve setting the pressure on the outlet side of the pump. These and other modifications may be made to the above identified disclosure without departing from the spirit and scope of the invention.

I claim:

1. A particle measuring instrument comprising a flow cell adapted to receive a flowing stream of liquid entraining particles to be measured, means to measure the size of particles passing through said flow cell, means defining a fluid flow channel extending from a source of liquid through said flow cell, a pump which will maintain a constant flow rate at a selected constant pressure differential across said pump connected in said flow channel to pump the liquid that flows through said flow channel, first pressure regulating means for controlling the pressure at the inlet side of said pump to be at a first predetermined value, and second pressure regulating means for controlling a pressure at the outlet side of said pump to be at a selected second predetermined value greater than said first value by said selected constant pressure differential.

2. A particle measuring instrument as recited in claim 1 wherein said pump comprises gear pump, and means to drive said gear pump at constant speed.

3. A particle measuring instrument as recited in claim 1 wherein said source of liquid is at a high pressure greater than said first predetermined value and wherein said first pressure regulating means steps the pressure down to said first predetermined value.

4. A particle measuring instrument as recited in claim 1 wherein said pump is downstream from said flow cell in said flow channel.

5. A particle measuring instrument as recited in claim 4 wherein said source of liquid may be at a high pressure greater than said first predetermined value or be at ambient pressure and further comprising means to selectively configure said flow channel downstream from said pump to pass through said second pressure regulating means to a discharge outlet or to bypass said second pressure regulating means to a discharge outlet to ambient pressure, the pressure drop from said source of liquid to the inlet side of said pump at said constant flow rate being equal to said constant pressure differential when said source of liquid is at ambient pressure, wherein said selected constant pressure differential is provided across said pump when said source of liquid is at ambient pressure and said flow path is configured to bypass said second pressure regulating means.

6. A particle measuring instrument as recited in claim 1 wherein a filter is provided between said flow cell and said pump to filter particles from said liquid.

7. A particle measuring instrument as recited in claim 6 wherein means are provided to measure the pressure differential across said pump and provide an indication of the measured pressure differential.

8. A particle measuring instrument as recited in claim 1 wherein said second pressure regulating means comprises a check valve designed to open when the pressure on the inlet side of said check valve reaches said second predetermined value.

9. A method of maintaining a constant flow rate through a flow cell of a particle measuring instrument from a source of liquid at a relatively high pressure comprising pumping said liquid flowing from said source through the flow cell with a pump of a type which will cause a constant flow rate when a constant pressure differential is maintained across the pump, maintaining the pressure at the inlet side of said pump at a first predetermined value below said high pressure and maintaining the pressure at the outlet side of said pump at a second predetermined value greater than said first predetermined value by said constant pressure differential.

10. A method as recited in claim 9 wherein said pump is a gear pump, and further comprising driving said gear pump at a constant speed.

11. A method as recited in claim 9 further comprising operating said pump to draw liquid from said source through said flow cell from downstream of said flow cell.

12. A method of maintaining a constant flow rate through a flow cell of a particle measuring instrument from a source of liquid which may be at a high pressure substantially above ambient pressure or may be at ambient pressure, comprising flowing liquid from said source through said flow cell and through a pump, said pump maintaining a constant rate of flow when the pressure differential across said pump is at a predetermined differential value, drawing liquid from said source through said flow cell from downstream of said flow cell with said pump to drop the pressure at the entrance to said pump to a predetermined differential value below said ambient pressure when said source is ambient pressure, maintaining the outlet pressure of said pump at ambient pressure when said source is at said ambient pressure, maintaining a first predetermined regulated pressure below said high pressure and above said ambient pressure at the inlet of said pump when said source is at said high pressure, and maintaining the pressure at the outlet side of said pump at a second predetermined value greater than said first predetermined regulated pressure by said predetermined differential value when said source is at said high pressure.

13. A method as recited in claim 12 wherein said pump is a gear pump and further comprising driving said gear pump at a constant speed.

14. A method as recited in claim 12 wherein the pressure at the outlet of said pump is maintained at said second predetermined value by connecting the flow from the outlet side of said pump to flow through a check valve when said source of liquid is at said high pressure and connecting the flow from the outlet of said pump to bypass said check valve when said source of liquid is at said ambient pressure.

* * * * *